United States Patent [19]

Hernandez

[11] 4,017,297

[45] Apr. 12, 1977

[54] PHOSPHONATES FOR THE CONTROL OF BINDWEED

[75] Inventor: Turney John Hernandez, Centerville, Del.

[73] Assignee: E. I. Du Pont de Nemours and Company, Wilmington, Del.

[22] Filed: Aug. 29, 1975

[21] Appl. No.: 608,907

[52] U.S. Cl. .................................................. 71/86
[51] Int. Cl.² ........................................ A01N 9/36
[58] Field of Search ....................................... 71/86

[56] References Cited

UNITED STATES PATENTS

| | | | |
|---|---|---|---|
| 3,627,507 | 12/1971 | Langsdorf, Jr. ...................... | 71/76 |
| 3,819,353 | 6/1974 | Langsdorf, Jr. ...................... | 71/76 |
| 3,846,512 | 11/1974 | Langsdorf ............................. | 71/76 |
| 3,849,102 | 11/1974 | Bucha et al. ......................... | 71/76 |

Primary Examiner—Lewis Gotts
Assistant Examiner—Catherine L. Mills

[57] ABSTRACT

This invention relates to the control of bindweed by applying to the locus of the bindweed a compound selected from compounds having the following formula:

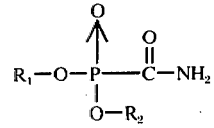

wherein $R_1$ and $R_2$ independently can be alkyl of 1 to 3 carbon atoms or allyl.

4 Claims, No Drawings

PHOSPHONATES FOR THE CONTROL OF BINDWEED

BACKGROUND OF THE INVENTION

U.S. Pat. Nos. 3,627,507, 3,819,353 and 3,846,512 teach the use of carbamoylphosphonates as plant growth regulants which are especially useful for controlling the growth of woody vegetation. There is, however, no direct mention that any of these compounds can control bindweed, nor is there any mention that the control of binweed can be done in a fashion that is not injurious to desirable crop plants. The control of bindweed is unexpected since it is a very difficult task and ordinarily requires the use of powerful herbicides, which would also tend to be quite injurious to desired crop plants such as tomatoes, etc.

SUMMARY OF THE INVENTION

In accordance with the instant invention, it has unexpectedly been discovered that certain phosphonates are capable of controlling bindweed. More specifically, the compounds of the instant invention control bindweed but tend not to injure crop plants such as wheat, tomatoes, soybean, corn and sugarbeets in the locus of the bindweed.

In a particular embodiment of the instant invention, the compounds of the invention are applied to an area infested with the bindweed immediately prior to planting of crops; subsequently, no substantial crop injury is caused by the compounds of the instant invention.

The compounds which are utilized, according to the instant invention, in order to control bindweed, have the following formula:

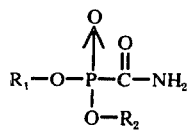

FORMULA I wherein $R_1$ and $R_2$ independently can be alkyl of 1 to 3 carbon atoms or allyl.

Preferred for their high level of biological activity are those compounds of Formula I wherein $R_1$ and $R_2$ are independently methyl or ethyl. Most preferred are the following compounds of Formula I:
  a. dimethyl carbamoylphosphonate, and
  b. diethyl carbamoylphosphonate.

DETAILED DESCRIPTION OF THE INVENTION

Binweed (*Convolvulus spp.*) is a noxious weed that infests many acres of cropland. Many compounds are known which can control bindweed; however, these compounds tend to leave residues which are toxic to crop plants. Unexpectedly, the compounds of Formula I can be applied to an area infested with bindweed just prior to planting crops, without crop injury. That is to say, crops may be planted immediately after an application of the compounds of Formula I without crop injury.

The compounds of Formula I are typically applied at rates of from four to twelve kg/ha, although rates of from two to twenty kg/ha may more generally be utilized.

The dialkyl carbamoylphosphonates which are useful in the method of this invention can be prepared by a variety of processes available in the literature. The process employed by Nylen, Chem. Ber. 57, 1023(1924), Reetz et al., J.A.C.S. 77, 3813–3816 (1955), Grisley, U.S. Pat. No. 3,005,010, and Bucha et al. U.S. Pat. No. 3,849,102, can be generally applied to the preparation of the compounds of formula I wherein $R_1$ and $R_2$ are identical. The process comprises treating an appropriate trialkyl phosphite with a chloroformate or thiolchloroformate and then treating the resulting dialkyl alkoxycarbonylphosphonate or alkylthiolcarbonylphosphonate with ammonia to give the desired carbamoylphosphonate. These reactions can be represented as follows:

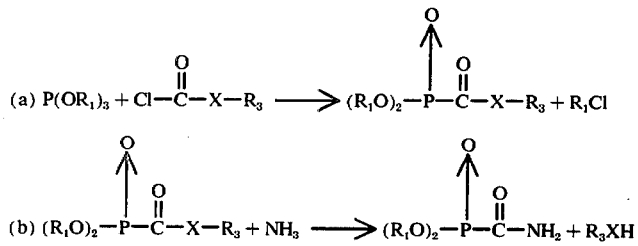

In equations (a) and (b) $R_1$ is defined as above, $R_3$ is lower alkyl, preferably methyl or ethyl and X is oxygen or sulfur. In most instances X will preferably be oxygen.

The starting materials of equation (a) above are commercially available or can be readily prepared using methods known to the art. The reaction between the dialkylalkoxycarbonylphosphonate and the ammonia described above is generally run at a temperature of from 20° to 150° C. A solvent is not necessary; but if a solvent is used, one which is inert to the reactants employed should be chosen. Suitable solvents include ethers, hydrocarbons or chlorinated hydrocarbons.

Illustrative of the phosphite esters which can be employed in the reaction are esters such as trimethyl phosphite and triethyl phosphite. "Mixed" phosphites can, of course, also be used, in which case "mixed" ester products can be obtained. Illustrative "mixed" phosphite esters include diethyl methyl phosphite, dimethyl ethyl phosphite and diisopropyl methyl phosphite.

Illustrative of the acid chlorides employed in the above reaction are methyl chloroformate, ethyl chloroformate, methyl triolchloroformate and ethyl thiolchloroformate.

Illustrative of the carbonylphosphonate intermediates which can be used as a starting material in the reaction of equation (b) to prepare the compounds of Formula I are dimethyl methoxycarbonylphosphonate, diallyl methoxycarbonylphosphonate, dipropyl ethoxycarbonylphosphonate, diethyl propoxycarbonylphosphonate, methyl ethyl ethoxycarbonylphosphonate and diethyl methylthiolcarbonylphosphonate.

The carbonylphosphonate ester intermediates generally are liquid products. Usually it is not necessary to purify them further after removal of the by-product alkyl halide and solvent. If desired, however, purification can be effected by distillation under reduced pressure. Purification and separation of the desired intermediate may be desirable where a "mixed" carbonylphosphonate is prepared. It will be understood that the term "mixed" carbonylphosphonate is used to identify those compounds which contain more than one ester group such as methyl ethyl ethoxycarbonylphosphonate.

In the procedure outlined in equation (b), the dialkyl alkoxycarbonylphosphonates can be reacted with ammonia with or without a solvent present. It is desirable that a solvent be employed where considerable heat of reaction is involved in the mixing of reactants. Generally, however, mixing can be effected without solvent present and external heating may be required to complete the reaction.

The compounds of Formula I generally are solids which are generally acceptable for use as bindweed control agents after removal of the by-product alcohol and solvent.

The preparation of the compounds of Formula I is further illustrated in the following Examples. Parts and percentages in the Examples are by weight unless otherwise specified.

EXAMPLE 1

One hundred and thirty parts of trimethyl phosphite are heated to 125° C. and treated with 100 parts of methyl chloroformate at a rate sufficient to maintain a reaction temperature of at least 100° C. After gas evolution stops, the residue is distilled to obtain 131 parts of dimethyl methoxycarbonylphosphonate, b.p. 83°–85° C./1.2 mm., $n_D^{25}$ = 1.4210.

Twenty parts of the above liquid are heated to 40° C. and 2.2 parts of anhydrous ammonia are added over a 2-hour period. The solidified reaction mass is essentially pure dimethyl carbamoylphosphonate, m.p. 150° C.

EXAMPLES 2 and 3

The procedure of Example 1 is repeated by substituting an equivalent amount of the indicated "Alkoxycarbonylphosphonate Ester" to produce the "Carbamoyl Product." These products are soluble in water, as well as in lower alcohols and ketones.

| Ex. | Alkoxycarbonyl- phosphonate Ester | Carbamoyl Product |
| --- | --- | --- |
| 2 | diethyl ethoxycarbonylphosphonate | diethyl carbamoylphosphonate |
| 3 | diisopropyl methoxycarbonylphosphonate | diisopropyl carbamoylphosphonate |

EXAMPLE 4

A slight excess (5–10%) of gaseous ammonia is introduced into a stirring mixture of 11 parts of diallyl methoxycarbonylphosphonate (from triallyl phosphite and methyl chloroformate) and 200 parts of tetrahydrofuran. The temperature increases from 25° to 28° C. spontaneously. The mixture is then heated to 35° C. and maintained at this temperature for 2 hours. The slightly hazy solution is filtered, and solvent is removed from the filtrate at 50° C. under reduced pressure (15 mm.). The residual solid is recrystallized from benzene, giving 6 parts of white crystalline diallyl carbamoylphosphonate, m.p. 91°–94° C.

Compositions of the present invention for control of bindweed containing at least one of the compounds of Formula I above may be prepared by admixing at least one of these compounds with known adjuvants or modifiers. The resulting compositions may be used in forms such as dusts, solutions, water-dispersible powders, dispersions and emulsions.

Compounds of Formula I may also be used with a carrier or diluent agent such as a finely divided solid, a solvent liquid of organic origin, water, a wetting agent, a dispersing agent, an emulsifying agent, or any suitable combination of these.

Compositions of the invention, especially liquids and wettable powders, may contain as a conditioning agent one or more surface-active agents in amounts sufficient to render a given composition containing the compounds of Formula I readily dispersible in water or in oil. By the term "surface-active agent", it is understood that wetting agents, dispersing agents, suspending agents and emulsifying agents are included. Suitable surface-active agents are set out, for example, in "Detergents and Emulsifiers Annual" (1972) by John W. McCutcheon, Inc. In general, about 0.1 to 10 percent by weight of the surface-active agent is present in the compositions of this invention, although usually the amount of surface-active agent in these compositions is a maximum of about 5 percent by weight, e.g., about 1–5, preferably about 0.5 to 3 percent by weight.

Among the formulations which are preferred are certain powders, water-soluble powders, certain dusts, certain emulsifiable oils, and solutions in certain solvents.

Wettable powders are water-dispersible compositions containing the active material, an inert solid extender, and usually one or more surfactants to provide rapid wetting and prevent heavy flocculation when suspended in water.

The inert extenders which should be used in the preferred wettable powders of this invention containing the compounds of Formula I are preferably of mineral origin and the surfactants are preferably anionic or non-ionic.

The classes of extenders most suitable for the wettable powder formulations of this invention are natural clays, diatomaceous earths, and synthetic mineral fillers derived from silica and silicate. Organic dusts can also be used as extenders. Among non-ionic and anionic surfactants, those most suitable for the preparation of the dry, wettable products of this invention are solid forms of compounds known to the art as wetters and dispersants. Occasionally a liquid, non-ionic compound classified primarily as an emulsifier may serve as both wetter and dispersant, but such types are usually avoided because of the difficulty in obtaining homogeneous distribution through the solid mass.

Most preferred fillers for this invention are kaolinites, montmorillonites and attapulgites. Preferred wetting agents are alkylbenzene- and alkylnaphthalene-sulfonates, sulfated fatty alcohols, amines or acid amides, long chain acid esters of sodium isethionate, esters of sodium sulfosuccinate, sulfated or sulfonated fatty acid esters, petroleum sulfonates, sulfonated vegetable oils and ditertiary acetylinic glycols. Preferred dispersants are methylcellulose, hydroxyethylcellulose, polyvinyl alcohol, sodium lignin sulfonates, polymeric alkylnaphthalene sulfonates, sodium naphthalenesulfonate, polymethylene bis-naphthalenesulfonate and sodium N-methyl-N-(long chain acid)-taurates.

Wetting and dispersing agents in these preferred wettable powder compositions of this invention are usually present at concentrations of from about 0.5 weight percent to 5 weight percent. The inert extender then completes the formulation. In some compositions small amounts of corrosion inhibitors and antifoam agents might be added at the expense of the inert extender.

Those compounds of the invention which are water soluble can be dissolved in water without any other additive present and the resultant aqueous solution can be used as is or can be further diluted with water and sprayed on the locus to be treated. In order to speed the solution rate, conditioners can be used such as wetting and dispersing agents as described above. Grinding can be employed to reduce the particle size and increase the surface area. Finely divided inert solid extenders can be blended into the formulation also. Upon extension with water the active component first disperses and then dissolves, leaving the inert solid in suspension. Depending upon the specific compound being used, aqueous concentrates up to 50–55% strength can be prepared.

Dusts are dense powder compositions which are intended for application in dry form, in accordance with the preferred compositions and methods of the invention. Dusts are characterized by their free-flowing and rapid settling properties so that they are not readily wind-borne to areas where their presence is not desired. They contain primarily an active material and a dense, free-flowing, solid extender.

Their performance is sometimes aided by the inclusion of a wetting agent, and convenience in manufacture frequently demands the inclusion of an inert, absorptive grinding aid. For the compounds of this invention, the inert extender may be either of vegetable or mineral origin, the wetting agent is preferably anionic or non-ionic, and suitable absorptive grinding aids are of mineral origin.

Preferred inert solid extenders for the dusts of this invention are micaceous talcs, pyrophyllite, dense kaolin clays, ground calcium phosphate rock such as that known as "Phosphodust" (a trademark of the American Agricultural Chemical Company), pulverized calcium carbonate, particularly the surface modified "CCC" diluent, and tobacco dust.

Preferred grinding aids are attapulgite clay, diatomaceous silica, synthetic fine silica and synthetic calcium and magnesium silicates. Preferred wetting agents are those previously listed under wettable powder formulations.

The inert solid extenders in the dusts of this invention are usually present in concentrations of from about 30 to 90 weight percent of the total composition. The grinding aid will usually constitute 5 to 50 weight percent of the composition, and the wetting agent will constitute from about 0 to 1.0 weight percent of the composition. Dust compositions can also contain other surfactants such as dispersing agents in concentrations of up to about 0.5 weight percent.

The wettable powders described above may also be used in the preparation of dusts. While such wettable powders could be used directly in dust form, it is more advantageous to dilute them by blending with the dense dust diluent. In this manner, dispersing agents, corrosion inhibitors, and anti-foam agents may also be found as components of a dust.

Emulsifiable oils are usually solutions of active material in solvents not miscible with water, together with surfactants.

For the compounds of this invention, emulsifiable oils can be made by mixing the active ingredient with a liquid carrier and surfactant or surfactants. Suitable carriers for the compounds of this invention are hydrocarbons (substituted or unsubstituted), and water immiscible ethers, esters, or ketones. Suitable surfactants are those anionic or non-ionic agents known to the art as emulsifying agents. Such compounds can be found listed by J.W. McCutcheon in "Detergents and Emulsifiers Annual" (1968).

Emulsifying agents most suitable for the compositions of this invention are, singly or in combinations, alkylaryl polyethoxy alcohols, alkyl- and alkylaryl polyether alcohols, polyoxyethylene sorbitol or sorbitan fatty acid esters, polyethylene glycol fatty esters, fatty alkylol amide condensates, amine salts of fatty alcohol sulfates plus long chain alcohols and oil soluble petroleum sulfonates, alkylphenoxy polyethoxy phosphates, and alkyloxy polyethoxy phosphate esters. Such emulsifying agents will usually comprise from about 3 to 10 weight percent of the total composition.

Thus, emulsifiable oil compositions of the present invention wil consist of from about 20 to 50 weight percent active material, about 40 to 75 weight percent liquid carrier, and about 3 to 10 weight percent emulsifier, as these terms are defined and used above.

While conventional applications of sprayable formulations have usually been made in a dilute form (for example, at a rate of about 200 liters per hectare or more), the compounds of this invention can also be applied at higher concentrations in the typical "Ultra-low-volume" (ULV) or "low-volume" applications from aircraft or ground sprayers. For this purpose wettable powders can be dispersed in small amounts of aqueous or non-aqueous carrier. Emulsifiable concentrates can be used directly or with minor dilution. Special compositions, particularly suitable for ULV applications, are solutions of finely divided suspensions in one or more carrier such as dialkylformamides, N-alkyl pyrrolidones, dimethyl sulfoxide, water, esters, ketones, glycols, glycol ethers and the like. Other suitable carriers include aromatic hydrocarbons (halogenated and nonhalogenated), aliphatic hydrocarbons (halogenated and nonhalogenated) and the like.

The following Examples are present to further illustrate the formulation and application of the compounds of this invention. Parts and percentages in the following Examples are by weight unless otherwise indicated.

EXAMPLE 5

A water soluble powder of the following formula is prepared:

| | |
|---|---|
| Dimethyl carbamoylphosphonate | 95.0% |
| Sodium dioctyl sulfosuccinate | 0.5% |
| Synthetic fine silica | 4.5% |

The above ingredients are blended together into a uniform mixture and hammer milled until most particles will pass a USS 40 mesh screen.

EXAMPLE 6

A water extendable liquid of the following formula is prepared:

| | |
|---|---|
| Diethyl carbamoylphosphonate | 25.0% |
| Dimethylformamide | 75.0% |

The diethyl carbamoylphosphonate is dissolved with stirring in the dimethylformamide.

The ability of the compounds of Formula I to control bindweed is illustrated by the following Example.

EXAMPLE 7

Twelve kilograms of the water-soluble powder formulation of Example 5 is dissolved in 1800 liters of water, and 0.25% of surfactant WK (dodecyl ether of polyethylene glycol) is added. This solution is sprayed uniformly on a 1 hectare of an area infested with bindweed to provide long-term control of bindweed.

EXAMPLE 8

An aqueous solution of the following formula is prepared:

| | |
|---|---|
| Diethyl carbamoylphosphonate | 40.0% |
| Dioctyl sulfosuccinate, Na salt | 0.5% |
| Water | 59.5% |

The composition is prepared by stirring the ingredients until solution is complete.

What is claimed is:

1. A method for the retardation of bindweed on cropland which comprises applying to the foliage of the bindweed a herbicidally-effective amount of a compound selected from compounds having the formula

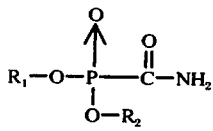

wherein $R_1$ and $R_2$ independently can be alkyl of 1 to 3 carbon atoms or allyl, and then proceeding immediately to plant crops on said cropland whereby there is substantially no injury to said crops.

2. The method of claim 1 wherein $R_1$ and $R_2$ are independently methyl or ethyl.

3. The method of claim 1 wherein the compound is dimethyl carbamoylphosphonate.

4. The method of claim 1 wherein the compound is diethyl carbamoylphosphonate.

* * * * *